(12) United States Patent
Schmand et al.

(10) Patent No.: US 12,385,997 B2
(45) Date of Patent: Aug. 12, 2025

(54) ARRANGEMENT OF PET DETECTORS FOR COMBINED PET/MR SYSTEMS

(71) Applicant: Siemens Medical Solutions USA, Inc., Malvern, PA (US)

(72) Inventors: Matthias J. Schmand, Lenoir City, TN (US); Paul Schleyer, Knoxville, TN (US); James L. Corbeil, Knoxville, TN (US); Vladimir Panin, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 396 days.

(21) Appl. No.: 18/004,186

(22) PCT Filed: Sep. 11, 2020

(86) PCT No.: PCT/US2020/070531
§ 371 (c)(1),
(2) Date: Jan. 4, 2023

(87) PCT Pub. No.: WO2022/055540
PCT Pub. Date: Mar. 17, 2022

(65) Prior Publication Data
US 2023/0288508 A1    Sep. 14, 2023

(51) Int. Cl.
*G01R 33/48* (2006.01)
*A61B 6/03* (2006.01)
(Continued)

(52) U.S. Cl.
CPC ............ *G01R 33/481* (2013.01); *A61B 6/037* (2013.01); *A61B 6/4266* (2013.01);
(Continued)

(58) Field of Classification Search
CPC ..... G01R 33/481; A61B 6/037; A61B 6/4266; A61B 6/4275; A61B 5/055; A61B 6/42;
(Continued)

(56) References Cited

U.S. PATENT DOCUMENTS

| 5,065,760 A | 11/1991 | Krause et al. |
| 2008/0061241 A1* | 3/2008 | Rietzel ................. A61B 6/4441 250/363.05 |
| 2018/0239037 A1 | 8/2018 | Yamaya et al. |

FOREIGN PATENT DOCUMENTS

| CN | 101528125 | 9/2009 |
| EP | 2843443 | 3/2015 |
| WO | 2020115299 | 6/2020 |

OTHER PUBLICATIONS

International Search Report for Corresponding PCT Application No. PCT/US2020/070531, dated May 28, 2021.

\* cited by examiner

*Primary Examiner* — Courtney D Thomas

(57) ABSTRACT

A PET system for a PET/MRI machine is disclosed. The PET system includes a PET detector assembly arranged to form a single gap aligned with the high-density support structure assembly and the shielded cable assembly that run along the patient bed in the PET/MRI machine. The PET detector arrangement maximizes the allowable diameter of the PET system within the MR magnet and ensures that the high-density material does not interfere with image acquisition. Further, various image reconstruction techniques compatible with the PET detector arrangement are described.

15 Claims, 4 Drawing Sheets

(51) Int. Cl.
 *A61B 6/42* (2024.01)
 *G06T 11/00* (2006.01)
(52) U.S. Cl.
 CPC .......... *A61B 6/4275* (2013.01); *G06T 11/006* (2013.01); *G06T 2211/424* (2013.01)
(58) Field of Classification Search
 CPC ... A61B 6/4417; A61B 6/4429; G06T 11/006; G06T 2211/424
 See application file for complete search history.

ARRANGEMENT OF PET DETECTORS FOR COMBINED PET/MR SYSTEMS

TECHNICAL FIELD

The present disclosure is generally directed to positron emission tomography (PET)/magnetic resonance imaging (MRI) systems. In one particular implementation, the present disclosure is directed to detector arrangements for PET/MRI systems.

BACKGROUND

PET/MRI is a hybrid imaging technology that uses MRI for soft tissue morphological imaging and PET for functional imaging. Typically, PET/MRI systems require the PET detectors to be positioned within the MR magnet and gradient coils, which limits the flexibility of the PET gantry design. PET systems consist of several rings of detectors which are usually arranged to minimize radial gaps between each detector because large gaps in the radial and/or azimuthal directions (i.e., transaxial gaps) can cause PET imaging artifacts. For PET/MR, it is also a requirement to maximize the diameter of the PET system within the MR magnet to produce the largest bore possible for receiving the patient. Given the physical constraints imposed by the MRI magnet and the gradient coils, it is sometimes not possible to choose the PET radius that minimizes the transaxial gap between the detectors, while also providing the maximum possible diameter for the PET systems. In particular, if a design was chosen that minimized the radial gap between the detectors, the detector arrangement would be either too large (in radius) to fit into the MRI system or too small (in radius) to be practical. Further, an overly small radius for the detector arrangement can result in blurrier data toward the transaxial edge of the field of view, resulting in inferior data quality.

Another issue inherent to MRI systems is that they commonly require high-density shielded cables for transmit and/or receive coils that run partly or entirely along the axial length of the patient table. Further, the support structure for the patient table can include other high-density materials. These high-density materials can cause PET photon attenuation and scatter issues that can lead to PET imaging artifacts. PET/MRI systems conventionally address the issues caused by these high-density materials by incorporating the structural rails and cable trays into the attenuation correction map of the patient table. However, scatter issues can still remain despite the attenuation correction map. Further, cables may also be moved or shifted during the used of the system, which creates potential uncertainties in the positioning of the high-density shielded cables. Accordingly, the cables are often omitted from the attenuation correction maps, which can result in PET imaging artifacts due to under-correction of the attenuation. For all high-density material inside the PET field of view, the PET detectors which are closest to the structures are affected the most.

Therefore, there is a need in the technical field for a PET detector arrangement that solves the various issues described above, including minimizing the radial gap between the PET detectors while maximizing the PET system diameter and compensating for the shielded cables and other high-density materials that run along the patient table.

SUMMARY

In one general aspect, the present disclosure is directed to a detector assembly for a PET/MRI machine comprising a bore configured to receive a patient therein, the detector assembly comprising: a set of n PET detectors arranged radially about the bore, wherein the plurality of PET detectors are arranged such that there is at least one non-uniform gap between the set of n PET detectors.

In another aspect, the present disclosure is directed to a PET/MRI machine comprising the aforementioned detector assembly.

In another aspect, the gap can be arranged such that it is aligned with the shielded cable assembly, the support structure assembly of the patient table, and/or other high-density materials associated with the PET/MRI machine.

FIGURES

The accompanying drawings, which are incorporated in and form a part of the specification, illustrate the embodiments of the invention and together with the written description serve to explain the principles, characteristics, and features of the invention. In the drawings.

DESCRIPTION

Figure 1:
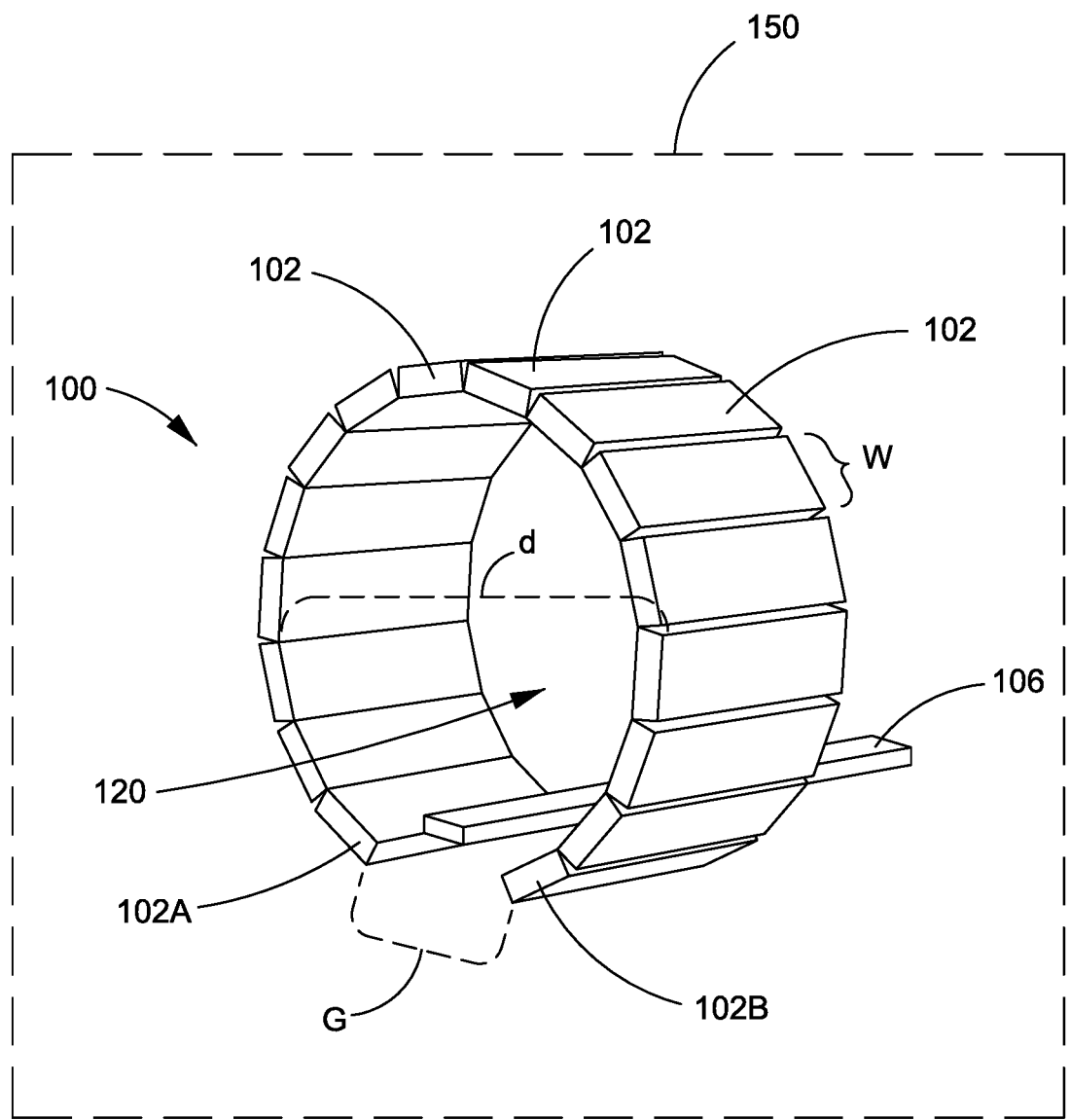
FIG. 1 depicts a diagram of a PET system for a PET/MRI machine in accordance with some embodiments.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

As noted above, it would be ideal for the gantry for the PET system in a PET/MRI machine to be as large as possible. Further, the PET system must be placed within the MR magnet and gradient coils. Still further, it is generally undesirable for there to be a significant radial gap between the PET detectors because significant gaps can create image quality issues. These and other competing concerns in the design of a PET system for a PET/MRI machine create two problems. First, one can design a PET system to either (i) have a radial gap between the PET detectors and have an acceptably sized opening or (ii) have no radial gap between the PET detectors and have a narrow opening. In other words, using a realistic number of PET detectors, one cannot simultaneously have no significant gap between the PET detectors and an appropriately sized opening. Second, the required placement of the PET system forces the high-density cables and/or support structures for the patient table to run through the field of view (FOV) of the PET system. It could theoretically be possible to specifically redesign and reconstruct each MRI machine to have a uniquely designed PET system based on the physical architecture of each MRI machine. However, this would be extremely labor intensive and expensive though and is not feasible in practice.

Described herein is an arrangement of PET detectors for combined PET/MRI systems that solves there issues. In one embodiment, the PET detectors can be arranged such that there is at least one non-uniform or non-periodic gap between the PET detectors. This differs from the prior art because prior art systems generally arrange the PET detectors uniformly (i.e., with regular or consistent gaps between the PET detectors or such that the PET detectors are arranged equidistant azimuthally) in order to aid the image reconstruction algorithms. In one embodiment, the PET detectors can be arranged such that there is one consolidated gap in the PET system. In other words, all of the gaps between the PET detectors are minimized to the maximum extent physically permitted by the PET system gantry and PET system hardware, except for a single consolidated gap between two of the PET detectors in the PET system. Further, the non-uniform or consolidated gap can be positioned such that it aligns with the high-density components extending along the patient bed. This is a convenient arrangement because these high-density components commonly cause interference in conventional PET systems. Also described herein are imaging reconstruction algorithms that are configured to handle one large gap as opposed to multiple smaller gaps between the PET detectors.

Referring now to FIG. 1, there is shown a diagram of a PET system 100 for a PET/MRI machine 150 in accordance with some embodiments. The PET system 100 includes a set of n PET detectors 102 that are arranged radially about a bore 120 of the PET/MRI machine 150. The bore 120 is sized, shaped, and otherwise configured to receive a patient therein for imaging. The PET detectors 102 can further be positioned within the magnet (not shown) of the PET/MRI machine 150. In the illustrated embodiment, there are sixteen PET detectors 102; however, this is embodiment is simply for illustrative purposes and no limitation on the number of PET detectors 102 in the PET system 100 is intended.

Figure 3:
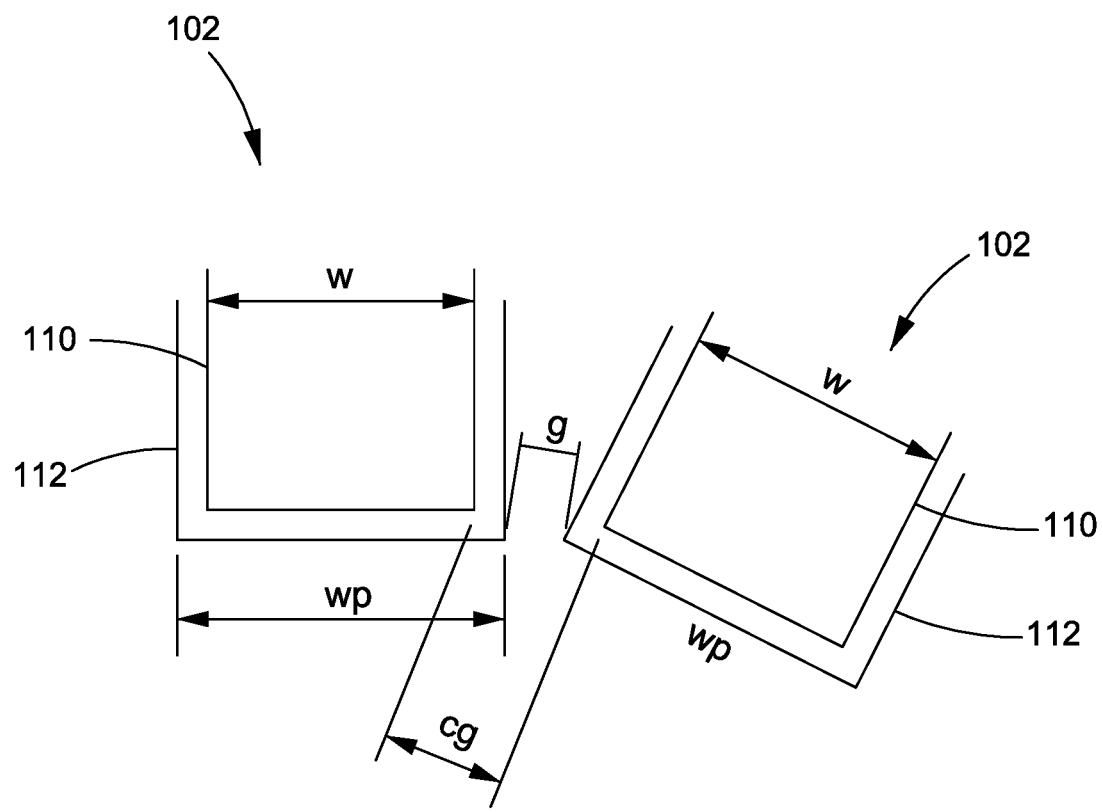
FIG. 3 depicts a diagram showing an arrangement of a pair of PET detectors in a PET system in accordance with some embodiments.

In one embodiment, the PET detectors 102 are arranged such that there is at least one non-uniform gap G between two of the PET detectors 102. In the illustrated embodiment, the PET detectors 102 are arranged such that they substantially abut each other (i.e., there are no significant gaps between the PET detectors 102), except for the gap G located between a first PET detector 102A and a second PET detector 102B from the collection or set of PET detectors. In another words, the gaps that would normally be presented between the PET detectors 102 in prior art PET systems are consolidated into the gap G, minimizing the individual gaps between the PET detectors 102 and maximizing the single, non-uniform gap G. It should be noted that the crystals of the PET detectors 102 require shielding (e.g., from visible light and electrical interference from other components of the PET system 100). The shielding, housing, and/or packaging of the PET detectors 102 will naturally force a small gap between the crystal blocks of two adjacent PET detectors 102 that could be equal to approximately a pixel width. Accordingly, what is meant by there being no significant gaps between the PET detectors 102 is that there are no gaps between the PET detectors 102 that exceed a pixel width. FIG. 3 depicts an illustrative arrangement between an adjacent pair of PET detectors 102 within the PET system 100. Each of the PET detectors 102 includes a crystal 110 having a width w and a corresponding housing or packaging 112 therefor having a width wp. Further, there exists both a gap g between the packaging 112 of the adjacent PET detectors 102 and a gap cg between the crystals 110 of the adjacent PET detectors 102. The goal with the various embodiments of the PET system 100 described herein is to arrange the PET detectors 102 such that (i) each crystal gap cp is less than or equal to a pixel width and (ii) each gap g is minimized (except for the gap G shown FIG. 1).

Figure 2A:
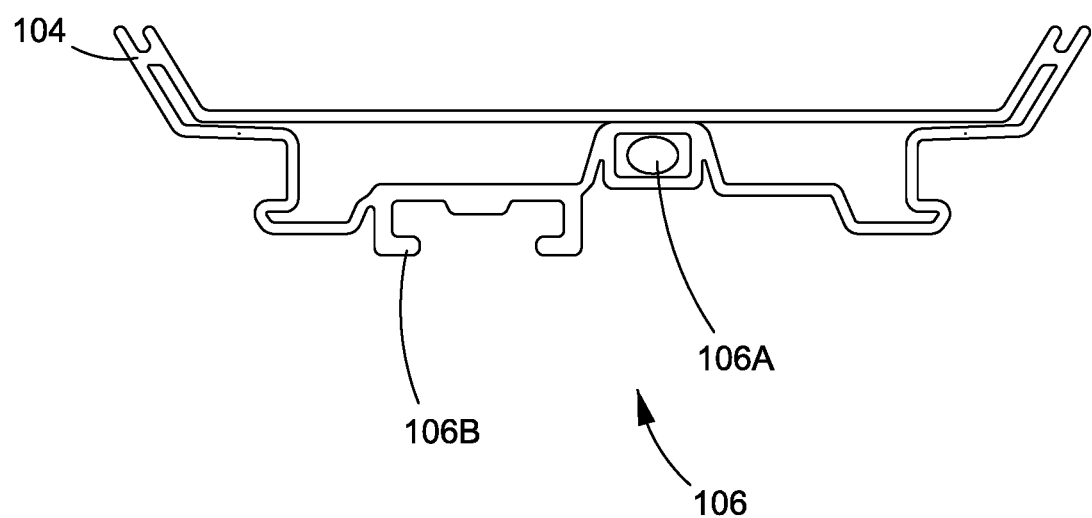
FIG. 2A depicts a sectional view of a patient bed for a PET/MRI machine in accordance with some embodiments.
Figure 2B:
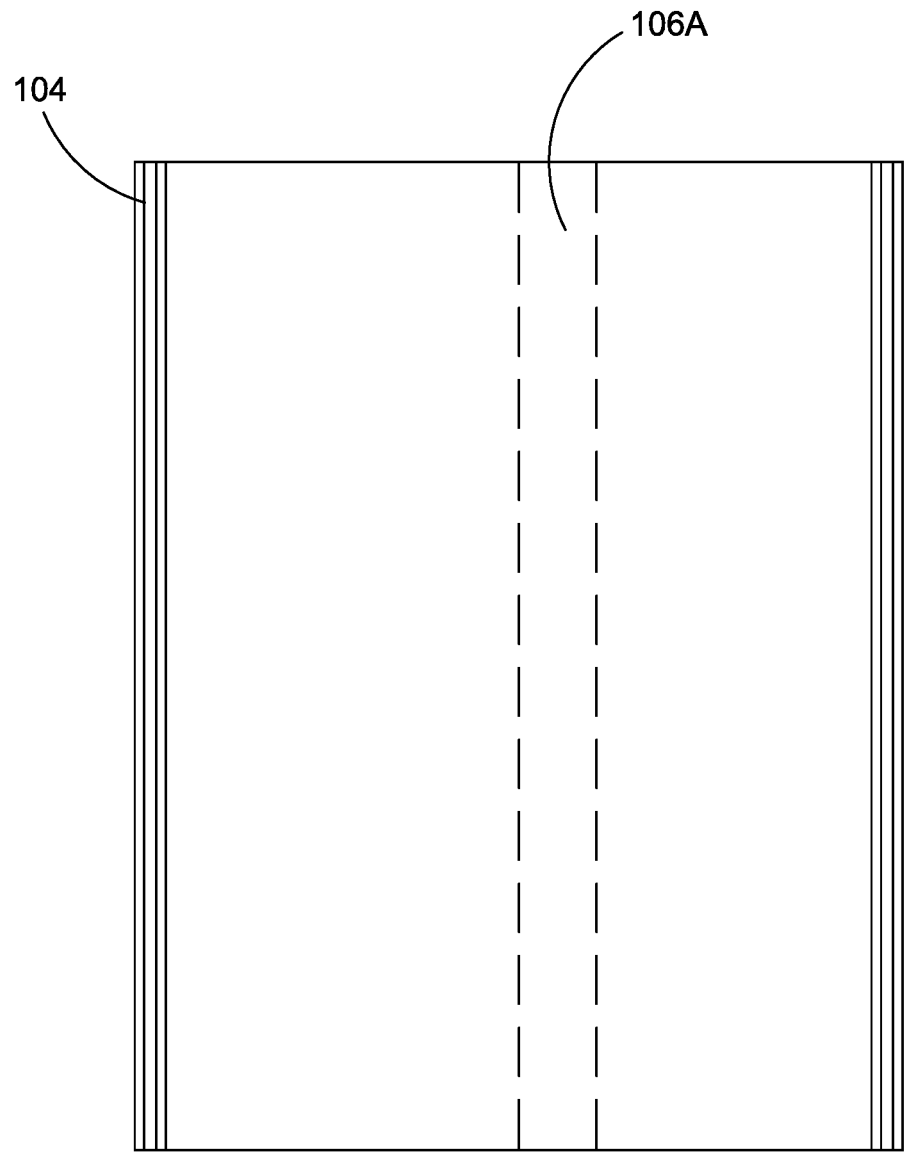
FIG. 2B depicts an underside view of a patient bed for a PET/MRI machine in accordance with some embodiments.

In one embodiment, the gap G can be positioned such that it is aligned with or otherwise corresponds to the position of high-density materials 106, which are generally associated with the patient bed 104 of the MRI machine 150. In other words, the gap G can be sized and positioned such that it encompasses the high-density materials 106 along the patient bed 104 so that the high-density materials 106 do not lie directly in front of any of the PET detectors 102, thereby lessening the interference caused by the high-density materials 106 on the PET system 100. The high-density materials 106 can include, for example, the shielded cable assembly 106A (as shown in FIGS. 2A and 2B) and/or the support structure assembly 106B (as shown in FIG. 2A) that extend along the length of the patient bed 104.

In one embodiment, the PET system 100 can be arranged in a generally circular shape having a diameter d. In one embodiment, the size of the gap G can be defined as follows:

$$G=C-n*wp'-n*g$$

where C is the circumference of the PET system 100, n is the number of PET detectors 102, g is the gap between the crystals 110, and wp' is the wp(radius). Accordingly, the size of the gap G can be defined based on the number n of PET detectors 102, the width or size of the PET detectors 102, and the circumference of the PET system 100 that is made up of the PET detectors 102. In another embodiment, the arrangement of the PET system 100 can be considered to be a polygon approximating the circumference C, instead of assuming a curved detector. Accordingly, in one embodiment, the size of the gap G can be defined as follows:

$$G=C-n*w-\varepsilon$$

where $\varepsilon$ is an error term accounting for the difference between the circumference C and the polygon approximating the circumference C. In one embodiment, the PET detectors 102 can have a set or consistent width w.

Given fixed geometries of the PET detectors 102 and MR magnet of the PET/MRI machine 150, the PET detectors 102 are arranged to maximize the allowable diameter of the PET system 100 within the MR magnet. Further, rather than distributing the PET detectors 102 such that there are radial gaps between each PET detector 102, as is generally done in the technical field, the gaps are instead consolidated to a single, larger gap G positioned at one radial location of the PET system 100. Further, the gap G can extend the entire axial length of the PET system 100. This arrangement allows all of the high-density materials 106 along the underside of the patient table 104 to be positioned directly within the gap G, thereby preventing them from interfering with image acquisition.

In various embodiments, an image reconstruction system can be configured to use iterative or analytical PET reconstruction methods using the PET system 100 described herein. In particular, iterative PET reconstruction methods can be used to compensate for the single large gap. During validation, a detector extending the full axial extent of an illustrative PET system (equating to ¹⁄₁₉th of the system's crystals) was removed from the listmode stream and normalization file and the PET system was tested using a Ge-68 cylindrical phantom. No imaging artifacts were evident in the reconstructed images and the reconstructed images appeared equivalent to images obtained with the same PET system with no detectors removed. Using analytical reconstruction methods such as Fourier rebinned-filtered back-projection (FORE+FBP) or direct inversion Fourier transform (DIFT), the gap G can be effectively filled without loss of spatial resolution, provided that sufficiently high resolution time of flight (TOF) information is available. In particular, including TOF information results in transaxially redundant information. Further, by using John's equation-based consistency conditions, the missing data in a large transaxial gap, such as the gap G described herein, can effectively be recovered by interpolation. This methodology for analytical reconstruction is detailed and demonstrated in "TOF sinogram missing data filling method based on John's equation consistency conditions," published on Jul. 1, 2011 at Fully three-dimensional image reconstruction in radiology and nuclear medicine by Panin et al., which is hereby incorporated by reference herein in its entirety.

The PET system 100 and associated image reconstruction techniques described herein provide several benefits. First, they reduce cost associated with manufacturing the PET/MRI machines 150 because they allow for existing MR magnet and gradient coil configurations and existing PET detector geometries to be used. Second, they provide the optimal diameter for the bore 120 because there is no requirement to reduce the diameter of the bore 120 to minimize gaps in the PET system 100, as with conventional systems. Third, they improve the image quality generated by the PET/MRI machine 100 because the described PET system 100 mitigates attenuation and scatter effects caused by the high-density materials 106 associated with the patient table 104, which is present in conventional PET systems. Fourth, placing the gap G such that it is aligned with the high-density materials 106 minimizes the attenuation and scatter effects caused by the high-density materials 106. Conventionally, the PET detector(s) 102A, 102B closest to the high-density materials 106 in the patient table 104 are most affected by attenuation and, therefore, these detectors 102A, 102B measure reduced counts. However, this arrangement addresses this issue.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure that are within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof.

Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A PET/MRI machine comprising:
   a bore configured to receive a patient therein; and
   a set of n PET detectors arranged radially about the bore;
   wherein the set of n PET detectors are arranged such that all radial gaps between adjacent PET detectors of the set of n PET detectors are less than or equal to a pixel width except for one non-uniform radial gap between two adjacent PET detectors of the set of n PET detectors.

2. The PET/MRI machine of claim 1, further comprising a support structure assembly configured to support a patient bed configured to fit within the bore, wherein the non-uniform gap is aligned with the support structure assembly.

3. The PET/MRI machine of claim 2, wherein the non-uniform gap is sized to encompass the support structure assembly such that the support structure assembly does not lie directly in front of any of the set of n PET detectors.

4. The PET/MRI machine of any one of claims 1-3, further comprising a shielded cable assembly extending along a patient bed configured to fit within the bore, wherein the non-uniform gap is aligned with the shielded cable assembly.

5. The PET/MRI machine of claim 4, wherein the non-uniform gap is sized to encompass the shielded cable assembly such that the shielded cable assembly does not lie within the field of view of any of the set of n PET detectors.

6. The PET/MRI machine of claim 1, wherein the set of n PET detector are arranged such that all gaps between adjacent PET detectors of the set of n PET detectors are uniform except for the non-uniform gap, the non-uniform gap comprising approximately 5% of a circumference of the set of n PET detectors.

7. The PET/MRI machine of any one of claims 1-3 and 6, wherein:
   the set of n PET detectors comprises a first PET detector and a second PET detector;
   the non-uniform gap comprises a gap G between the first PET detector and a second PET detector that is defined by:

$$G = C - n*w - \varepsilon$$

where C is a circumference of the n PET detectors, w is a width of each of the n PET detectors, and $\varepsilon$ is an error term.

8. The PET/MRI machine of any one of claims 1-3, wherein the PET/MRI machine is configured to reconstruct an image using an image reconstruction algorithm, the image reconstruction algorithm comprising at least one of a Fourier rebinned-filtered backprojection or a direct inversion Fourier transform.

9. A detector assembly for a PET/MRI machine comprising a bore configured to receive a patient therein, the detector assembly comprising:
   a set of n PET detectors arranged radially about the bore;
   wherein the set of n PET detectors are arranged such that all radial gaps between adjacent PET detectors are uniform are less than or equal to a pixel width except for one non-uniform radial gap between two adjacent PET detectors of the set of n PET detectors.

10. The detector assembly of claim 9, wherein the non-uniform gap is aligned with a support structure assembly of the PET/MRI machine, the support structure assembly configured to support a patient bed configured to fit within the bore.

11. The detector assembly of claim 10, wherein the one non-uniform gap is sized to encompass the support structure assembly such that the support structure assembly does not lie directly in front of any of the set of n PET detectors.

12. The detector assembly of any one of claims 9-11, wherein the one non-uniform gap is aligned with a shielded cable assembly extending along a patient bed configured to fit within the bore.

13. The detector assembly of claim 12, wherein the non-uniform gap is sized to encompass the shielded cable assembly such that the shielded cable assembly does not lie within the field of view of any of the set of n PET detectors.

14. The detector assembly of claim 9, wherein the set of n PET detectors are arranged such that all radial gaps between adjacent PET detectors of the set of n PET detectors are uniform except for the non-uniform radial gap, the non-uniform radial gap having a width approximately equal to a width of one PET detector of the set of n PET detectors.

15. The detector assembly of any one of claims 9-11 and 14, wherein:
   the set of n PET detectors comprises a first PET detector and a second PET detector;
   the non-uniform gap comprises a gap G between the first PET detector and a second PET detector that is defined by:

$$G = C - n*w - \varepsilon$$

where C is a circumference of the n PET detectors, w is a width of each of the n PET detectors, and $\varepsilon$ is an error term.

* * * * *